United States Patent
Nassif et al.

(10) Patent No.: US 11,654,212 B2
(45) Date of Patent: May 23, 2023

(54) INJECTABLE COLLAGEN SUSPENSIONS, THE PREPARATION METHOD THEREOF, AND THE USES THEREOF, PARTICULARLY FOR FORMING DENSE COLLAGEN MATRICES

(71) Applicants: UNIVERSITE PIERRE ET MARIE CURIE (PARIS 6), Paris (FR); CENTRE NATIONAL DE LA RECHERCHE SCIENTIFIQUE, Paris (FR)

(72) Inventors: Nadine Nassif, Paris (FR); Francisco Miguel Moreira Martins Fernandes, Paris (FR); Cedric Boissiere, Villebon sur Yvette (FR); Clement Sanchez, Bures-sur-Yvette (FR); Marie-Madeleine Giraud-Guille, Paris (FR)

(73) Assignees: UNIVERSITE PIERRE ET MARIE CURIE (PARIS 6), Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/558,787

(22) PCT Filed: Mar. 17, 2016

(86) PCT No.: PCT/FR2016/050599
§ 371 (c)(1),
(2) Date: Sep. 15, 2017

(87) PCT Pub. No.: WO2016/146954
PCT Pub. Date: Sep. 22, 2016

(65) Prior Publication Data
US 2018/0071430 A1 Mar. 15, 2018

(30) Foreign Application Priority Data

Mar. 17, 2015 (FR) ...................................... 1552200

(51) Int. Cl.
| | |
|---|---|
| *A61L 27/24* | (2006.01) |
| *A61L 27/50* | (2006.01) |
| *A61L 27/54* | (2006.01) |
| *A61L 27/52* | (2006.01) |
| *A61K 8/02* | (2006.01) |
| *A61K 8/14* | (2006.01) |
| *A61K 38/39* | (2006.01) |
| *A61K 8/65* | (2006.01) |
| *A61Q 19/08* | (2006.01) |
| *A61K 8/60* | (2006.01) |
| *C08J 3/12* | (2006.01) |

(52) U.S. Cl.
CPC .............. *A61L 27/24* (2013.01); *A61K 8/022* (2013.01); *A61K 8/025* (2013.01); *A61K 8/14* (2013.01); *A61K 8/606* (2013.01); *A61K 8/65* (2013.01); *A61K 38/39* (2013.01); *A61L 27/50* (2013.01); *A61L 27/52* (2013.01); *A61L 27/54* (2013.01); *A61Q 19/08* (2013.01); *C08J 3/122* (2013.01); *A61K 2800/412* (2013.01); *A61K 2800/654* (2013.01); *A61K 2800/91* (2013.01); *A61L 2300/232* (2013.01); *A61L 2300/236* (2013.01); *A61L 2300/252* (2013.01); *A61L 2300/402* (2013.01); *A61L 2300/428* (2013.01); *A61L 2400/06* (2013.01); *A61L 2430/06* (2013.01); *A61L 2430/34* (2013.01); *A61L 2430/38* (2013.01); *C08J 2389/00* (2013.01)

(58) Field of Classification Search
None
See application file for complete search history.

(56) References Cited

U.S. PATENT DOCUMENTS

| | | | |
|---|---|---|---|
| 3,393,080 A | 7/1968 | Erdi et al. | |
| 4,131,650 A * | 12/1978 | Braumer ............... | A61K 8/0212 128/DIG. 8 |
| 4,565,580 A | 1/1986 | Miyata et al. | |
| 5,405,757 A * | 4/1995 | Prockop ................. | C07K 14/78 435/366 |
| 5,428,024 A * | 6/1995 | Chu ........................ | A61L 27/24 514/17.2 |
| 7,241,309 B2 * | 7/2007 | Castro ................... | A61L 27/227 623/1.47 |
| 8,785,389 B2 * | 7/2014 | Brown .................... | A61L 27/38 514/774 |
| 2003/0082224 A1 * | 5/2003 | Noujaim ................ | A61K 9/167 424/423 |
| 2004/0137051 A1 | 7/2004 | Ehringer et al. | |
| 2007/0254041 A1 * | 11/2007 | Drapeau ............. | A61L 27/3608 424/550 |
| 2013/0190479 A1 | 7/2013 | Tanaka et al. | |
| 2013/0338636 A1 * | 12/2013 | Chan .................. | A61B 17/0057 604/506 |
| 2015/0023911 A1 * | 1/2015 | Schilling ................ | A61K 38/00 424/85.2 |

FOREIGN PATENT DOCUMENTS

| | | | | |
|---|---|---|---|---|
| CN | 104059954 A | 9/2014 | | |
| EP | 2599820 A1 | 6/2013 | | |
| GB | 2274458 A | 7/1994 | | |
| JP | 2006-16381 A | 1/2006 | | |
| WO | WO-2013113821 A1 * | 8/2013 | ............. | A61L 31/16 |
| WO | 2015/053629 A1 | 4/2015 | | |

OTHER PUBLICATIONS

Nilforoushzadeh, M. A. et al. "Soft tissue augmentation by autologous cultured fibroblasts . . . " Journal of Research in Medical Sciences : The Official Journal of Isfahan University of Medical Sciences, 2010, 15(3), 167-1714, accessed via https://www.ncbi.nlm.nih.gov/pmc/articles/PMC3082806/, p. 1-4. (Year: 2010).*

(Continued)

*Primary Examiner* — Erin E Hirt
(74) *Attorney, Agent, or Firm* — Nixon & Vanderhye (57) ABSTRACT

Disclosed is the preparation of injectable collagen suspensions, to the method for preparing the suspensions, and to the uses thereof, particularly for forming dense collagen matrices.

6 Claims, 5 Drawing Sheets

(56) References Cited

OTHER PUBLICATIONS

Feng, E. et al. "Comparison of Collagen from cultured human fibroblasts . . . " Pediatric Research, Abstract only, 1977, 11, 455 (See abstract 500) (Year: 1977).*
Chan et al. J. of Controlled Release, 2008, 129(2), 135-143. (Year: 2008).*
Nagai et al. J. Mater. Sci. Mater. Med. 2010, 21(6) 1891-8 (Year: 2010).*
Hussila Keshaw, et al., Microporous collagen spheres produced via thermally induced phase separation for tissue regeneration, Acta Biomaterialia, 2010, pp. 1158-1166, vol. 6, Elsevier Ltd.
Wolfgang Friess, Collagen—biomaterial for drug delivery, European Journal of Pharmaceutics and Biopharmaceutics, 1998, pp. 113-136, vol. 45, Elsevier Science B.V.
Fu Yin Hsu, et al., Microspheres of hydroxyapatite/reconstituted collagen as supports for osteoblast cell growth, Biomaterials, 1999, pp. 1931-1936, vol. 20, Elsevier Science Ltd.
International Search Report for PCT/FR2016/050599 dated Aug. 9, 2016, 3 pages.
Written Opinion of the ISA for PCT/FR2016/050599 dated Aug. 9, 2016, 8 pages.
Tanizaki et al., "Cellular characterization of thrombocytes in Xenopus laevis with specific monoclonal antibodies," Experimental Hematology, 2015, vol. 43, pp. 125-136.
FR Search Report issued in FR Patent Application No. 1552200 dated Oct. 14, 2015.

* cited by examiner

T= 0     T= 48H in DMEM

INJECTABLE COLLAGEN SUSPENSIONS, THE PREPARATION METHOD THEREOF, AND THE USES THEREOF, PARTICULARLY FOR FORMING DENSE COLLAGEN MATRICES

The present invention relates to the preparation of injectable collagen suspensions, the preparation method thereof, and uses thereof, particularly for forming dense collagen matrices.

The proportion of collagens in the human body is predominant, with fibrillar collagens being involved in the structuring of extracellular matrices. Type I collagen is found in abundance in the supporting tissues, vessels, dermis, tendons and ligaments, cornea and bone. It therefore remains a prime candidate for a natural polymer constituent of tissue substitutes due to its haemostatic properties, its low immunogenicity, and its implications in cell behaviour. Thus, in the present context, different types of substitutes based on collagen have already been proposed for industrial applications. Numerous methods have been proposed in the literature for the formulation of collagen (Friess et al., *Eur. J. Pharma. Biopharma.* 1998, 45, 113-136), however these matrices generally have a low collagen concentration.

The use of collagen particles from acid-soluble collagen as a means for obtaining concentrated collagenous materials has been proposed by numerous methods. Morson (GB2274458) demonstrated that acid-soluble collagen can be spray dried in order to obtain particles that can be used in the clarification of fermented beverages. Nevertheless, the working conditions specified in this application, in particular drying temperatures of 120° C., involve denaturing of the triple helices of collagen.

Other works (EP2599820) propose methods for precipitating collagen based on the use of hydrophilic organic solvents, such as ethanol, acetone and diethyl ether. By means of this method, the authors were able to precipitate micron-sized collagen particles. Nevertheless, the use of organic solvents, and more particularly the presence of traces of these compounds in the materials obtained, can pose problems in respect of toxicity in the event of injection of the formulations.

Formulations in the form of beads based on emulsion techniques in a water/oil mixture (Hsu et al., *Biomaterials*, 1999, 20, 1931-1936) or water/organic solvents mixture (U.S. Pat. No. 4,565,580) in conditions of non-denaturation of the protein have also been proposed. However, traces of oil or of solvents are associated with the beads formed. An alternative is the technique of thermally induced phase separation (TIPS), wherein the drops of the solution are introduced into a bath of liquid nitrogen, followed by a step of lyophilisation (Keshaw, et al., *Acta. Biomater.* 2010, 6, 1158-1166). In all cases, the fragility of the collagen beads formed leads to a step of crosslinking by chemical agents (aldehydes, carbodiimides), of which the toxicity poses a problem. Indeed, in these works, the molecules of type I collagen are present in solution at low concentration (approximately 1 mg/ml), at acidic pH.

Thus, one object of the present invention is to provide collagen suspensions forming dense collagen matrices in vivo.

Another object of the present invention is to provide collagen suspensions forming, in vivo, collagen matrices that are stable over time, particularly are resistant over time to collagenases.

Another object of the present invention is to provide collagen suspensions of elevated concentration which can be easily injected due to their rheological properties.

Another object of the present invention is to provide collagen suspensions forming implantable dense collagen matrices after treatment.

Another object of the present invention is to provide suspensions of non-denatured, uncrosslinked collagen, these suspensions being devoid of contaminants such as solvents, emulsifiers or chemical reagents.

The invention consequently relates to a solid spherical or spheroid particle formed fundamentally of non-denatured and uncrosslinked collagen, the diameter of said particle being from 0.05 to 20 µm, in particular from 0.25 to 10 µm, more particularly from 0.4 µm to 3 µm.

The term spheroid means a solid of which the shape assimilates that of a sphere.

The term diameter means the diameter of the sphere or the greatest diameter of the spheroid.

This diameter can be measured for example by electron microscopy or by dynamic light scattering.

The expression "formed fundamentally of collagen" means a particle comprising more than 90% by mass of collagen, in particular more than 91%, 92%, 93%, 94%, 95%, 96%, 97%, 98%, 99%, 99.5% or 99.9%.

The term "non-denatured" means a collagen of which the secondary structure of α-triple helices is preserved.

Figure 3:
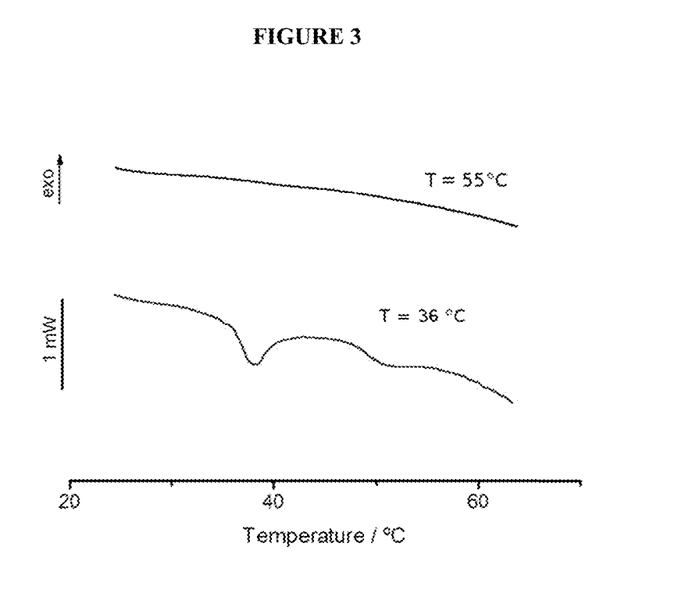
FIG. 3 illustrates the differential scanning calorimetry of collagen powders obtained by spray drying a solution of acid-soluble solution (0.7 mg·mL-1) in acetic acid (0.5M) at 36 and 55° C. The samples were analysed under conditions of controlled humidity so as to allow the identification of the denaturation processes of the collagen.
Figure 4:
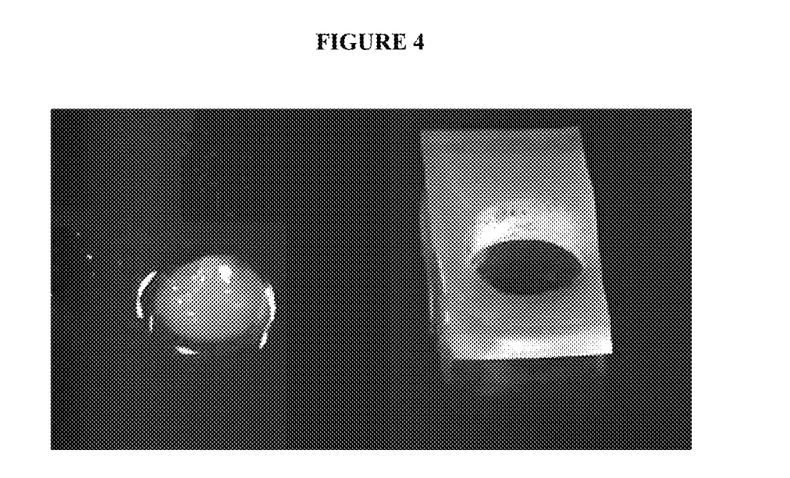
FIG. 4 shows a collagen gel obtained by diffusion of ammonia vapours in a PDMS mould filled with a collagen coacervate at a concentration of 5.6 mg·ml$^{-1}$ in the presence of ATP.
Figure 5:
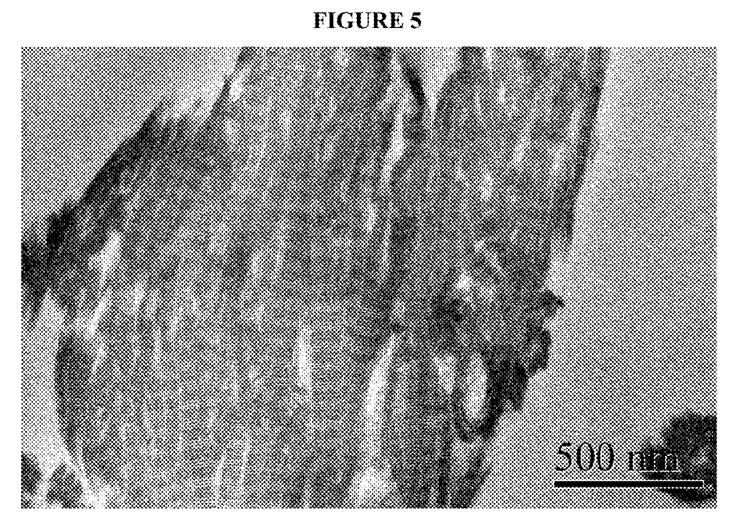
FIG. 5 is an image recorded by transmission electron microscopy of a cut obtained by ultramicrotomy of a sample synthesised from acid-soluble collagen at a concentration of 5.6 mg·ml$^{-1}$ after coacervation by ATP and fibrillogenesis induced by ammonia vapours. The sample was fixed in an aqueous solution of dehydrated glutaraldehyde, dried to the supercritical point, enclosed in an epoxy matrix and contrasted by uranyl acetate.
Figure 6:
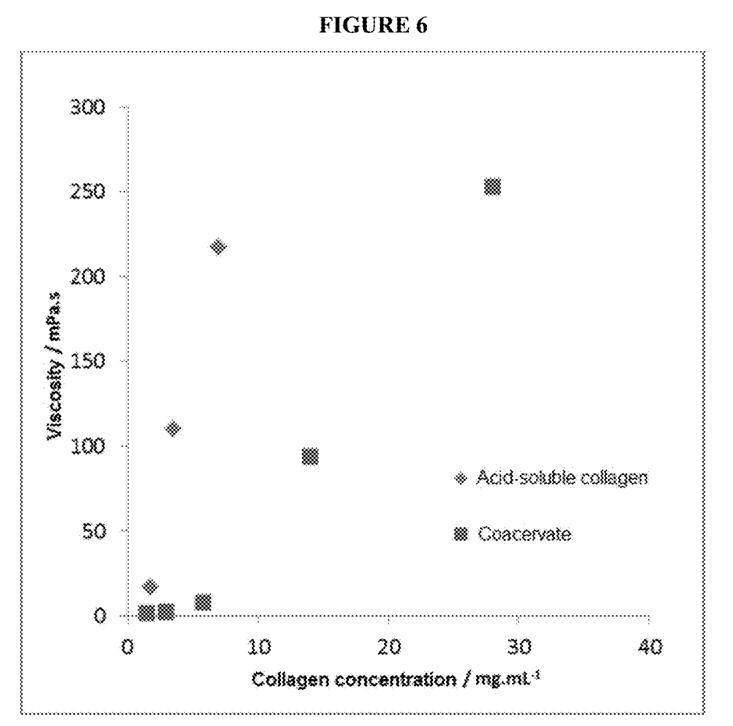
FIG. 6 shows the viscosity of solutions of acid-soluble collagen and of collagen coacervates according to Example 8 as a function of the total collagen concentration.

The non-denatured or denatured nature of collagen can be observed for example by calorimetric analysis. Denatured collagen has a calorimetric profile characteristic of a denatured protein (gelatin), with no sign of organised macromolecular domains (FIG. 3).

The term "uncrosslinked" means a collagen in which there are no chemical crosslinking bonds, whether these bonds are the result of chemical modifications, such as treatment by glutaraldehyde, or physical modifications.

The absence of crosslinking can be determined for example by electrophoresis.

In an especial embodiment of the invention, the invention relates to a particle containing no contaminants, such as organic solvents, emulsifiers or chemical reagents, in particular crosslinking agents.

The term crosslinking agents means, preferably, diphenylphosphorylazide (DPPA), glutaraldehyde (GAD), a carbodiimide, such as the carbodiimide 1-ethyl-3-(3-dimethylaminopropyl) carbodiimide (EDC), or N-hydroxysuccinimide (NHS).

The source of collagen is irrelevant.

In particular, the collagen can be obtained in accordance with the following protocol: a solution of type I collagen is prepared from Wistar rat tail tendons. After excision in a laminar flow cabinet, the tendons are washed in a sterile saline phosphate buffer solution. The tendons are then immersed in a solution of 4M NaCl in order to remove the remaining intact cells and precipitate some of the proteins of elevated molecular weight. After washing by the saline phosphate buffer solution, the tendons are solubilised in a sterile 500 mM acetic acid solution. The solution obtained is clarified by centrifugation at 41000 g for 2 hours. The proteins other than the collagen are precipitated selectively in an aqueous solution of 300 mM NaCl and removed by centrifugation at 41000 g for 3 hours. The collagen is recovered from the supernatant by precipitation in a solution of 600 mM NaCl followed by centrifugation at 3000 g for 45 minutes. The pellets obtained are solubilised in an aqueous solution of 500 mM acetic acid, then dialysed in the same solvent in order to remove the NaCl ions. The solution is held at 4° C. and centrifuged at 41000 g for 4 hours prior to use.

The protocol above can also be applied to other types of collagen.

In accordance with an advantageous embodiment, the invention relates to a particle as defined above, in which the collagen has a molecular mass from 200 to 450 KDa.

In accordance with an advantageous embodiment, the invention relates to a particle as defined above, in which the collagen is selected from collagens of type I, II, III, V, XI, XXIV, XXVII, and mixtures thereof.

In accordance with an advantageous embodiment, the invention relates to a particle as defined above, in which the collagen is present at least in part in the form of fibrils, preferably in the form of striated collagen fibrils, formed by collagen triple helices and in which the periodicity is 67 nm, said fibrils forming domains in which the fibrils are aligned in a preferential direction over a large distance, for example a distance greater than 200 nm, 500 nm, 1 µm or 5 µm, and/or isotropic domains in which they are not ordered.

The term fibrils means an ordered arrangement of collagen molecules giving rise to the formation of anisotropic structures.

The term striated fibrils means fibrils having a repetitive pattern of striations when observed by transmission electron microscopy, after addition of a contrast agent such as uranyl acetate.

In accordance with an advantageous embodiment, the invention relates to a particle as defined above, comprising less than 10% by mass of solvent, particularly acetic acid, in particular less than 9%, 8%, 7%, 6%, 5%, 4%, 3%, 2%, 1%, 0.5% or 0.1%.

The density of the particles is characterised by the assembly of the uncrosslinked collagen molecules, of which the intermolecular distance is less than 10 nm, preferably less than 5 nm, and in particular less than 2 nm.

In accordance with an advantageous embodiment, the invention relates to a particle as defined above, which particle is birefringent.

A birefringence signal can be observed for example by polarised light microscopy.

The invention also relates to a powdered composition comprising or consisting of particles as defined above.

The term powdered composition means the powder formed by the particles of the invention, as defined above.

In accordance with an advantageous embodiment, the invention relates to a powdered composition as defined above, which is devoid of emulsifier, in particular surfactants or oils.

In an especial embodiment of the invention, the invention relates to a powdered composition as defined above containing no contaminants such as organic solvents, emulsifiers or chemical reagents, in particular crosslinking agents.

The invention also relates to a method for preparing a powdered composition as defined above, comprising a step of atomisation of an acidic solution of non-denatured and uncrosslinked collagen at a temperature below approximately 40° C., in particular below approximately 39° C., 38° C. or 37° C., to obtain the powdered composition.

During this step of atomisation, an aerosol is formed by spraying the collagen solution, which is dried so as to form the powdered composition.

In accordance with an advantageous embodiment, the invention relates to a method as defined above, in which the concentration of the collagen solution is from 0.1 to 10 mg/ml.

In accordance with an advantageous embodiment, the invention relates to a method as defined above, in which the acid is acetic acid,
said aqueous solution being formed in particular of water, acid and non-denatured and uncrosslinked collagen,
the acidic collagen solution having particularly an acetic acid concentration of from 0.01 to 1000 mM.

The powdered compositions according to the invention can be alternatively placed in suspension in an aqueous solution, an acidic collagen solution, or a suspension of vesicles, which will be defined further below.

The invention also relates to a suspension comprising or consisting of a powdered composition as defined above, in an aqueous solution.

Surprisingly, the suspensions according to the invention can be easily injected into a tissue by way of a 27, 30 or 32 gauge needle, even at a high collagen concentration, that is to say at a collagen concentration greater than 10, 20, 30, 40, 50, 60, 70, 80, 90 or 100 mg per ml of suspension.

The aqueous solution is in particular a saline phosphate buffer.

In accordance with an advantageous embodiment, the invention relates to a suspension as defined above, in which said aqueous solution is a solution of acid-soluble collagen.

The term solution of acid-soluble collagen means any collagen solution of which the pH is below 7, in particular aqueous solutions comprising collagen and acetic acid.

Thus, in this case, a powdered collagen composition according to the present invention is placed in suspension in a solution itself containing collagen.

Said collagen suspension has a collagen concentration greater than the collagen solution to which the collagen particles are added.

In accordance with an advantageous embodiment, the invention relates to a suspension as defined above, further containing vesicles comprising non-denatured and uncrosslinked collagen, ATP and an aqueous phase,
the aqueous phase of the vesicles and the aqueous solution of the suspension being in particular of the same kind, in particular identical.

Said collagen suspension has a collagen concentration greater than the suspension of vesicles, as defined further below, to which the collagen particles are added.

In accordance with an advantageous embodiment, the invention relates to a suspension as defined above, in which the collagen concentration is from 0.1 to 200 mg per ml of suspension, in particular from 1 to 200 mg per ml of suspension, especially from 10 to 200 mg per ml of suspension, even more especially from 10 to 75 mg per ml of suspension.

The term collagen concentration means the total collagen concentration of the suspension, that is to say of the particles, and, as the case may be, of the aqueous solution or of the vesicles.

In accordance with an advantageous embodiment, the invention relates to a suspension as defined above, which can be injected into a tissue by way of a 27, 30 or 32 gauge needle.

The invention also relates to a cosmetic composition containing a suspension as defined above, or a powdered composition as defined above.

In accordance with an advantageous embodiment, the invention relates to a cosmetic composition as defined above, further comprising one or more additives selected from anaesthetics, hyaluronic acid, elastins, vitamins and platelet-rich plasma, ions, precursors of a mineral phase, proteoglycans, glycosaminoglycan, and non-fibrillar collagen types.

In accordance with an advantageous embodiment, the invention relates to a cosmetic composition in which said suspension is a suspension comprising or consisting of a powdered composition as defined above, in an aqueous solution of acid-soluble collagen.

The invention also relates to a pharmaceutical composition containing, by way of active substance, a suspension as defined above, or a powdered composition as defined above.

In accordance with an advantageous embodiment, the invention relates to a pharmaceutical composition in which said suspension is a suspension comprising or consisting of a powdered composition as defined above, in an aqueous solution of acid-soluble collagen.

The cosmetic and pharmaceutical compositions of the present invention are in particular non-immunogenic or weakly immunogenic.

The invention also relates to a method for preparing a dense collagen fibrillar matrix in gel form comprising a step in which a suspension as defined above is exposed to conditions making it possible to increase the pH of said suspension to a value greater than 7.

The term fibrillar matrix means a physical gel formed by striated collagen fibrils.

The term dense fibrillar matrix means particularly a birefringent fibrillar matrix.

In addition, a dense fibrillar matrix is characterised by the assembly of collagen molecules of which the intermolecular distance is less than 10 nm, preferably less than 5 nm, and in particular less than 2 nm, the intermolecular distance being particularly from 1.2 to 1.8 nm.

A birefringence signal can be observed for example by polarised light microscopy.

In accordance with an advantageous embodiment, the invention relates to a method as defined above, in which the dense collagen fibrillar matrix in gel form comprises striated collagen fibrils formed by collagen triple helices and in which the periodicity is 67 nm, said fibrils forming domains in which the fibrils are aligned in a preferential direction over a large distance and/or isotropic domains in which they are not ordered,
said non-denatured and uncrosslinked collagen being in particular type I collagen.

Surprisingly, fibrillar matrices comprising fibrils in which the periodicity is 67 nm are obtained, even from suspensions having a low collagen concentration, for example suspensions containing 7 mg of collagen per ml of suspension.

The invention also relates to a method for preparing a dense collagen fibrillar matrix in gel form comprising a step in which a suspension as defined above is exposed to conditions making it possible to increase the ionic force of the suspension to a value at which the dense collagen fibrillar matrix in gel form is formed, for example by being contacted with a physiological medium, in particular extracellular liquid.

The invention also relates to a method for preparing a dense collagen fibrillar matrix in gel form comprising a step in which a suspension as defined above is exposed to conditions making it possible to increase the pH of said suspension to a value greater than 7 and to increase the ionic force of the suspension to values at which the dense collagen fibrillar matrix in gel form is formed, for example by being contacted with a physiological medium, in particular extracellular liquid.

The invention also relates to a dense collagen fibrillar matrix in gel form obtainable by the method as defined above.

The invention also relates to a physiologically compatible, absorbable or non-absorbable framework, comprising a dense collagen fibrillar matrix in gel form as defined above.

The dense collagen fibrillar matrices in gel form and the frameworks of the present invention are in particular non-immunogenic or weakly immunogenic.

The invention also relates to the use of a suspension as defined above for cosmetic filling of wrinkles.

The invention also relates to a method for cosmetic treatment of wrinkles of a subject, comprising administration, in particular by injection, of a suspension as defined above, to said subject.

The invention also relates to a suspension as defined above, or a powdered composition as defined above, for use thereof in the repair of tissue.

In accordance with an advantageous embodiment, the invention relates to a suspension as defined above, or a powdered composition as defined above, for use thereof in the repair of cartilage or an intervertebral disc.

In accordance with an advantageous embodiment, the invention relates to a suspension as defined above, or a powdered composition as defined above, for use thereof in the repair of joints.

In accordance with an advantageous embodiment, the invention relates to a suspension as defined above, or a powdered composition as defined above, for use thereof as filling material, particularly in plastic surgery, urogynaecological surgery, laryngoplasty, or following percutaneous surgery.

The invention also relates to an implantable medical device comprising or consisting of a dense collagen fibrillar matrix in gel form as defined above, or of a framework as defined above, said device being in particular an intervertebral disc prosthesis.

The invention also relates to a vesicle comprising or consisting of non-denatured and uncrosslinked collagen, ATP and an aqueous phase,
the diameter of said vesicle being from 0.1 μm to 10 μm, in particular from 0.2 μm to 5 μm, especially from 0.5 μm to 2 μm, even more especially approximately 1 μm.

The term vesicle means a flexible droplet.

The term ATP means adenosine-5'-triphosphate in neutral form or in any one of its charged forms.

The term diameter means the diameter of the sphere or the greatest diameter of the spheroid.

This diameter can be measured for example by microscopy or by dynamic light scattering.

The term "non-denatured" means a collage of which the secondary structure of α-triple helices is preserved.

The non-denatured or denatured nature of collagen can be observed for example by calorimetric analysis. Denatured collagen has a calorimetric profile characteristic of a denatured protein (gelatin), with no sign of organised macromolecular domains (FIG. 3).

The term "uncrosslinked" means a collagen in which there are no chemical crosslinking bonds, whether these bonds are the result of chemical modifications, such as treatment by glutaraldehyde, or physical modifications.

The absence of crosslinking can be determined for example by electrophoresis.

In an especial embodiment of the invention, the invention relates to a particle containing no contaminants, such as organic solvents, emulsifiers or chemical reagents, in particular crosslinking agents.

The term crosslinking agents means preferably diphenylphosphorylazide (DPPA), glutaraldehyde (GAD), a carbodiimide, such as the carbodiimide 1-ethyl-3-(3-dimethylaminopropyl) carbodiimide (EDC), or N-hydroxysuccinimide (NHS).

The source of collagen is irrelevant.

In particular, the collagen can be obtained in accordance with the following protocol: a solution of type I collagen is prepared from Wistar rat tail tendons. After excision in a laminar flow cabinet, the tendons are washed in a sterile saline phosphate buffer solution. The tendons are then immersed in a solution of 4M NaCl in order to remove the remaining intact cells and precipitate some of the proteins of elevated molecular weight. After washing by the saline phosphate buffer solution, the tendons are solubilised in a sterile 500 mM acetic acid solution. The solution obtained is clarified by centrifugation at 41000 g for 2 hours. The proteins other than the collagen are precipitated selectively in an aqueous solution of 300 mM NaCl and removed by centrifugation at 41000 g for 3 hours. The collagen is recovered from the supernatant by precipitation in a solution of 600 mM NaCl followed by centrifugation at 3000 g for 45 minutes. The pellets obtained are solubilised in an aqueous solution of 500 mM acetic acid, then dialysed in the same solvent in order to remove the NaCl ions. The solution is held at 4° C. and centrifuged at 41000 g for 4 hours prior to use.

The protocol above can also be applied to other types of collagen.

In accordance with an advantageous embodiment, the invention relates to a vesicle as defined above, in which the collagen has a molecular mass from 200 to 450 KDa.

In accordance with an advantageous embodiment, the invention relates to a vesicle as defined above, in which the collagen is selected from collagens of type I, II, III, V, XI, XXIV, XXVII, and mixtures thereof.

In accordance with an advantageous embodiment, the invention relates to a vesicle as defined above, in which the aqueous phase is acidic,
said aqueous phase being especially formed of water and acid,
said aqueous phase comprising in particular acetic acid, in particular at a concentration of from 0.00001 M to 1 M,
the pH of said aqueous phase being from 2.0 to 5.5, preferably from 2.0 to 4.0.

The term aqueous phase means an aqueous phase of which the pH is below 7.

In accordance with an advantageous embodiment, the invention relates to a vesicle as defined above, in which the collagen is in segment long spacing (SLS) form.

The term "segment long spacing form" (SLS form) means a stacking pattern of the collagen in which lateral aggregates are produced. Each aggregate has a length of approximately 300 nm, and the collagen molecules are all aligned.

In accordance with an advantageous embodiment, the invention relates to a vesicle as defined above, which is birefringent.

A birefringence signal can be observed for example by polarised light microscopy.

The invention also relates to a suspension comprising or consisting of vesicles as defined above, in an aqueous solution.

Thus, the vesicles in suspension are coacervates in suspension in said aqueous solution. These coacervates are flexible droplets, of which the collagen concentration is at least twice that of said aqueous solution.

In accordance with an advantageous embodiment, the invention relates to a suspension as defined above, in which said aqueous solution is acidic,
said aqueous solution being in particular formed of water and acid,
said aqueous solution comprising in particular acetic acid, particularly at a concentration of from 0.00001 M to 1 M,
the pH of said aqueous phase being from 2.0 to 5.5, preferably from 2.0 to 4.0.

The term acidic solution means a solution of which the pH is below 7.

In accordance with an advantageous embodiment, the invention relates to a suspension as defined above, in which the aqueous phase of the vesicles and the aqueous solution of the suspension are of the same kind, in particular identical.

In accordance with an advantageous embodiment, the invention relates to a suspension as defined above, which is devoid of emulsifier, in particular surfactants or oils.

In accordance with an advantageous embodiment, the invention relates to a suspension as defined above, further comprising solid spherical or spheroid particles formed fundamentally of non-denatured and uncrosslinked collagen,
the diameter of said particles being from 0.05 to 20 μm, in particular from 0.25 to 10 μm, especially from 0.4 μm to 3 μm.

The spherical or spheroid particles are as defined above.

Said collagen suspension has a collagen concentration greater than the suspension devoid of solid spherical or spheroid particles.

In accordance with an advantageous embodiment, the invention relates to a suspension as defined above, in which the collagen concentration is from 0.1 to 200 mg per ml of suspension, in particular from 1 to 200 mg per ml of suspension, especially from 10 to 200 mg per ml of suspension, even more especially from 40 to 200 mg per ml of suspension.

The term collagen concentration means the total concentration of collagen of the suspension, that is to say of the vesicles, of the aqueous solution and, as the case may be, of the solid spherical or spheroid particles.

In accordance with an advantageous embodiment, the invention relates to a suspension as defined above, in which the viscosity is from 1.7 to 253 mPa·s for collagen concentrations of from 1.45 to 28 mg per ml of suspension, respectively.

The viscosity can be determined at 50 Hz on an Anton Parr MCR 302 rheometer in rotational viscometer mode using a cone-plane geometry, at 25° C. and at atmospheric pressure. The shear rate used for these measurements is 50 $s^{-1}$.

Surprisingly, the suspensions according to the invention can be easily injected into a tissue, by way of a 27, 30 or 32 gauge needle, even at a high collagen concentration, that is to say at a collagen concentration greater than 10, 20, 30, 40, 50, 60, 70, 80, 90 or 100 mg per ml of suspension.

In accordance with an advantageous embodiment, the invention relates to a suspension as defined above, in which the collagen/ATP ratio is from 0.1 to 10 during the contacting step.

In accordance with an advantageous embodiment, the invention relates to a suspension as defined above, which can be injected into a tissue by way of a 27, 30 or 32 gauge needle.

The invention also relates to a method for preparing a suspension as defined above, comprising a step of contacting, with stirring, an aqueous solution of non-denatured and uncrosslinked collagen with ATP in order to obtain said suspension.

The ATP can be provided in free form or in the form of a corresponding salt, for example the disodium salt of ATP.

In accordance with an advantageous embodiment, the invention relates to a method as defined above, in which the collagen/ATP mass ratio is from 0.1 to 10 during the contacting step.

In accordance with an advantageous embodiment, the invention relates to a method as defined above, in which the stirring is performed at a rate of from 200 to 2400 revolutions per minute, in particular for 5 to 60 seconds.

In accordance with an advantageous embodiment, the invention relates to a method as defined above, comprising, after the contacting step, a step of concentration of the suspension, in particular by centrifugation of the suspension in order to obtain a pellet and a supernatant, then by removal of all or some of the supernatant obtained at the end of the centrifugation of the suspension, in order to obtain a concentrated suspension.

In accordance with an advantageous embodiment, the invention relates to a method as defined above, comprising:
a step of contacting, with stirring, an aqueous solution of non-denatured and uncrosslinked collagen with ATP, in order to obtain a suspension;
a step of concentration of the suspension, in particular by centrifugation of the suspension, in order to obtain a pellet and a supernatant, then by removal of all or part of the supernatant obtained at the end of the centrifugation of the suspension, in order to obtained a concentrated suspension.

The invention also relates to a cosmetic composition containing a suspension of vesicles comprising non-denatured and uncrosslinked collagen, ATP and an aqueous phase, in an aqueous solution,
the diameter of the vesicles being in particular from 0.1 μm to 10 μm.

In accordance with an advantageous embodiment, the invention relates to a cosmetic composition as defined above, further comprising one or more additives selected from anaesthetics, hyaluronic acid, elastins, vitamins and platelet-rich plasma, ions, precursors of a mineral phase, proteoglycans, glycosaminoglycan, or non-fibrillar collagen types.

In accordance with an advantageous embodiment, the invention relates to a cosmetic composition in which said suspension further comprises solid spherical or spheroid particles formed fundamentally of non-denatured and uncrosslinked collagen,
the diameter of said particles being from 0.05 to 20 μm, in particular from 0.25 to 10 μm, especially from 0.4 μm to 3 μm.

The invention also relates to a pharmaceutical composition containing, by way of active substance, a suspension of vesicles comprising non-denatured and uncrosslinked collagen, ATP and an aqueous phase, in an aqueous solution, the diameter of the vesicles being in particular from 0.1 μm to 10 μm.

In accordance with an advantageous embodiment, the invention relates to a pharmaceutical composition in which said suspension further comprises solid spherical or spheroid particles formed fundamentally of non-denatured and uncrosslinked collagen, the diameter of said particles being from 0.05 to 20 μm, in particular from 0.25 to 10 μm, especially from 0.4 μm to 3 μm.

The cosmetic and pharmaceutical compositions of the present invention are in particular non-immunogenic or weakly immunogenic.

The invention also relates to a method for preparing a dense collagen fibrillar matrix in gel form comprising a step in which a suspension of vesicles comprising non-denatured and uncrosslinked collagen, ATP and an aqueous phase, in an aqueous solution, is exposed to conditions making it possible to increase the pH of said suspension to a value greater than 7, the diameter of the vesicles being in particular from 0.1 μm to 10 μm.

The term fibrils means an ordered arrangement of collagen molecules giving rise to the formation of anisotropic structures.

The term striated fibrils means fibrils having a repetitive pattern of striations when observed by transmission electron microscopy, after addition of a contrast agent such as uranyl acetate.

The term dense fibrillar matrix means particularly a birefringent fibrillar matrix.

A birefringence signal can be observed for example by polarised light microscopy.

In addition, a dense fibrillar matrix is characterised by the assembly of collagen molecules of which the intermolecular distance is less than 10 nm, preferably less than 5 nm, and in particular less than 2 nm, the intermolecular distance being particularly from 1.2 to 1.8 nm.

In accordance with an advantageous embodiment, the invention relates to a method as defined above, in which the dense collagen fibrillar matrix in gel form comprises striated collagen fibrils formed by collagen triple helices and in which the periodicity is 67 nm, said fibrils forming domains in which the fibrils are aligned in a preferential direction over a large distance, for example a distance greater than 200 nm, 500 nm, 1 μm or 5 μm, and/or isotropic domains in which they are not ordered,
said method comprising a step in which a suspension of vesicles comprising non-denatured and uncrosslinked collagen, in particular fibrillar collagen, preferably type I collagen, ATP and an aqueous phase, in an aqueous solution, is exposed to conditions making it possible to increase the pH of said suspension to a value greater than 7.

Quite surprisingly, fibrillar matrices comprising fibrils in which the periodicity is 67 nm have been obtained from vesicles of collagen comprising collagen in SLS form.

The invention also relates to a method for preparing a dense collagen fibrillar matrix in gel form comprising a step in which a suspension of vesicles comprising non-denatured and uncrosslinked collagen, ATP and an aqueous phase, in an aqueous solution, is exposed to conditions making it possible to increase the ionic force of the suspension to a value at which the dense collagen fibrillar matrix in gel form is formed, for example by being contacted with a physiological medium,
the diameter of the vesicles being in particular from 0.1 μm to 10 μm.

The invention also relates to a method for preparing a dense collagen fibrillar matrix in gel form comprising a step in which a suspension of vesicles comprising non-denatured and uncrosslinked collagen, ATP and an aqueous phase, in an aqueous solution, is exposed to conditions making it possible to increase the pH of said suspension to a value greater than 7 and to increase the ionic force of the suspension to values at which the dense collagen fibrillar matrix in gel form is formed, for example by being contacted with a physiological medium, the diameter of the vesicles being in particular from 0.1 μm to 10 μm.

The invention also relates to a dense collagen fibrillar matrix in gel form obtainable by the method as defined above.

The invention also relates to a physiological compatible, absorbable or non-absorbable framework, comprising a dense collagen fibrillar matrix in gel form as defined above.

The dense collagen fibrillar matrices in gel form and the frameworks of the present invention are in particular non-immunogenic or weakly immunogenic.

The invention also relates to the use of a suspension of vesicles comprising or consisting of non-denatured and uncrosslinked collagen, ATP and an aqueous phase, in an aqueous solution, for cosmetic filling of wrinkles,
the diameter of the vesicles being in particular from 0.1 µm to 10 µm.

The invention also relates to a method for cosmetic treatment of wrinkles of a subject, comprising the administration, in particular by injection, of a suspension of vesicles comprising or consisting of non-denatured and uncrosslinked collagen, ATP and an aqueous phase, in an aqueous solution, to said subject,
the diameter of the vesicles being in particular from 0.1 µm to 10 µm.

The invention also relates to a suspension of vesicles comprising or consisting of non-denatured and uncrosslinked collagen, ATP and an aqueous phase, in an aqueous solution, for use thereof in the repair of tissue,
the diameter of the vesicles being in particular from 0.1 µm to 10 µm.

In accordance with an advantageous embodiment, the invention relates to a suspension as defined above, for use thereof in the repair of cartilage or an intervertebral disc.

In accordance with an advantageous embodiment, the invention relates to a suspension as defined above, for use thereof in the repair of joints.

In accordance with an advantageous embodiment, the invention relates to a suspension as defined above, for use thereof as filling material, particularly in plastic surgery, urogynaecological surgery, laryngoplasty, or following percutaneous surgery.

The invention also relates to an implantable medical device comprising or consisting of a dense collagen fibrillar matrix in gel form as defined above, or of a framework as defined above, said device being in particular an intervertebral disc prosthesis.

EXAMPLES

Example 1: Injectable Suspension of Collagen Microparticles (50 mg per mL) Obtained By Spraying and Dispersed in a Solution of Acid-Soluble Collagen (2 mg Per mL)

1.1 Obtaining a Solution of Acid-Soluble Collagen.

A solution of type I collagen is prepared from Wistar rat tail tendons. After excision in a laminar flow cabinet, the tendons are washed in a sterile saline phosphate buffer solution. The tendons are then immersed in a solution of 4M NaCl in order to remove the remaining intact cells and precipitate some of the proteins of elevated molecular weight. After washing by the saline phosphate buffer solution, the tendons are solubilised in a sterile 500 mM acetic acid solution. The solution obtained is clarified by centrifugation at 41000 g for 2 hours. The proteins other than the collagen are precipitated selectively in an aqueous solution of 300 mM NaCl and removed by centrifugation at 41000 g for 3 hours. The collagen is recovered from the supernatant by precipitation in a solution of 600 mM NaCl followed by centrifugation at 3000 g for 45 minutes. The pellets obtained are solubilised in an aqueous solution of 500 mM acetic acid, then dialysed in the same solvent in order to remove the NaCl ions. The solution is held at 4° C. and centrifuged at 41000 g for 4 hours prior to use.

1.2 Preparation of a Dry Powder from Non-Denatured Collagen.

A collagen solution with a concentration of 7 mg per mL is diluted in ultra-pure water (resistivity greater than 18.2 MΩ per cm) to obtain a collagen solution at a concentration of 1 mg per mL dissolved in an aqueous solution of 71 mM acetic acid. The solution thus obtained is dried in an atomiser ("spray drier" Buchi B290). The rate of injection of the collagen solution, limited to 1 ml per minute, is controlled by an automatic syringe pump connected to the nozzle of the drying instrument. The temperature of the nozzle is held at 36° C., and the internal temperature of the system, measured between the drying column and the particle collection cyclone, is maintained throughout the process between 26 and 31° C. The flow of air responsible for the shearing of the droplets at the outlet of the nozzle is 1052 L per hour. The suction power, which controls the drying of the droplets between the outlet of the nozzle and the collector, is fixed at 75% of the maximum capacity of the drying system (30 m$^3$ per hour). The particles thus formed are collected by a high-performance cyclone.

1.3 Preparation of a Suspension Obtained by Dispersion of the Collagen Powder in a Solution of Acid-Soluble Collagen A fraction of the powder thus obtained of mass 5.0 mg is dispersed in 100 µL of solution of acid-soluble collagen at an initial concentration of 2 mg per mL. The final collagen concentration of the suspension is 52 mg per ml. The suspension obtained after initial manual stirring and 30 seconds of stirring under vortex (2400 revolutions per minute) can be aspirated by a syringe equipped with a 27 gauge needle. The suspension has a white colour and a homogeneous macroscopic appearance.

Example 2: Injectable Suspension of Collagen Microparticles (7 mg per mL) Obtained by Spray Drying and Dispersed in a Solution of Acid-Soluble Collagen (7 mg Per mL)

2.1 Preparation of a Dry Powder of Non-Denatured Collagen.

Figure 1:
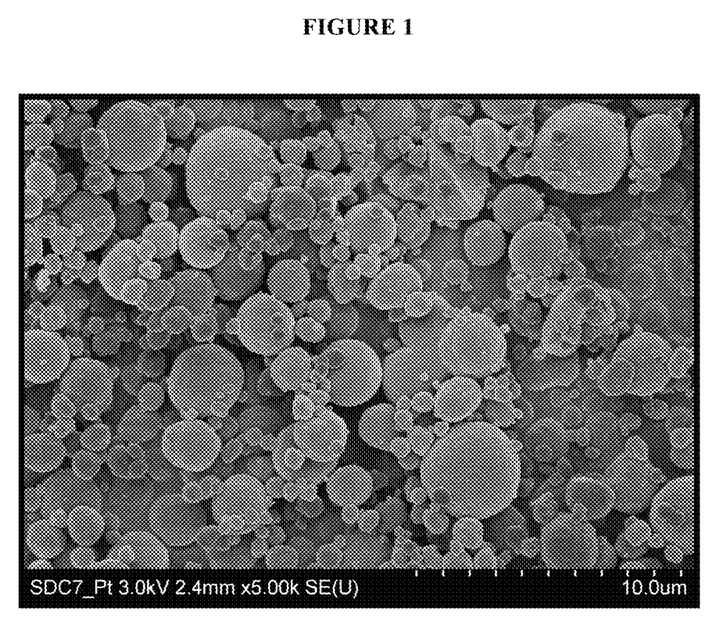
FIG. 1 shows collagen microparticles obtained by spray drying a solution of acid-soluble collagen (7 mg per mL) in acetic acid (0.5M) at 36° C.

A collagen solution is obtained in accordance with Example 1.1 with a concentration of 7 mg per mL. This solution is dried in an atomiser ("spray drier" Buchi B290). The rate of injection of the collagen solution, limited to 1 ml per minute, is controlled by an automatic syringe pump connected to the nozzle of the drying instrument. The temperature of the nozzle is held at 36° C., and the internal temperature of the system, measured between the drying column and the particle collection cyclone, is maintained throughout the process between 26 and 31° C. The flow of air responsible for the shearing of the droplets at the outlet of the nozzle is 1052 L per hour. The suction power, which controls the drying of the droplets between the outlet of the nozzle and the collector, is fixed at 75% of the maximum capacity of the drying system (30 m$^3$ per hour). The particles thus formed are collected by a high-performance cyclone. (FIG. 1).

2.2 Preparation of a Suspension Obtained by Dispersion of the Collagen Powder in a Solution of Acid-Soluble Collagen.

A fraction of the powder thus obtained of mass 7.0 mg is dispersed in 1 mL of solution of acid-soluble collagen at an initial concentration of 7 mg per mL. The final collagen concentration of the suspension is 14 mg per ml. The suspension obtained after initial manual stirring and 30 seconds of stirring under vortex (2400 revolutions per minute) can be aspirated by a syringe equipped with a 27 gauge needle. The suspension has a white colour and a homogeneous macroscopic appearance.

2.3 Fibrillogenesis Induced by Exposure to Ammonia Vapours.

After injection of the suspension in the closed PDMS mould, the assembly is exposed to ammonia vapours to promote fibrillogenesis. After 24 hours, the gel thus formed is demoulded, with no significant change in volume.

Example 3: Injectable Suspension of Collagen Microparticles (7 mg Par mL) Obtained by Spraying and Dispersed in a Saline Phosphate Buffer 3.1 Preparation of a Suspension Obtained by Dispersion of a Collagen Powder in a Saline Phosphate Buffer.

A dry collagen powder is obtained in accordance with Example 2.2. A fraction of the powder thus obtained of mass 7.0 mg is dispersed in 1 mL of saline phosphate buffer. The final collagen concentration of the suspension is 7 mg per ml. The suspension obtained after initial manual stirring and 30 seconds of stirring under vortex (2400 revolutions per minute) can be aspirated by a syringe equipped with a 27 gauge needle. The suspension has a white colour and a homogeneous macroscopic appearance. The suspension is then injected into a 70 µL cylindrical PDMS mould.

3.2 Fibrillogenesis Induced by Exposure to Ammonia Vapours.

After injection of the suspension in the closed PDMS mould, the assembly is exposed to ammonia vapours to promote fibrillogenesis. After 24 hours, the gel thus formed is demoulded, with no significant change in volume.

Example 4: Injectable Suspension of Collagen Microparticles (40 mg Par mL) Obtained by Spraying and Dispersed in a Saline Phosphate Buffer 4.1 Preparation of a Suspension Obtained by Dispersion of the Collagen Powder in a Saline Phosphate Buffer A suspension of collagen microparticles is obtained in accordance with Example 3.2. A fraction of the powder thus obtained of mass 40 mg is dispersed in 1 mL of saline phosphate buffer. The final collagen concentration of the suspension is 40 mg per ml.

4.2 After injection of the suspension in the closed PDMS mould, the assembly is exposed to ammonia vapours to promote fibrillogenesis. After 24 hours, the gel thus formed is demoulded, with no significant change in volume.

Example 5: Obtaining Collagen Microparticles by Spraying from a Solution of Acid-Soluble Collagen at a Concentration of 2.1 mg Per mL 5.1 Preparation of a Dry Powder of Non-Denatured Collagen.

Figure 2:
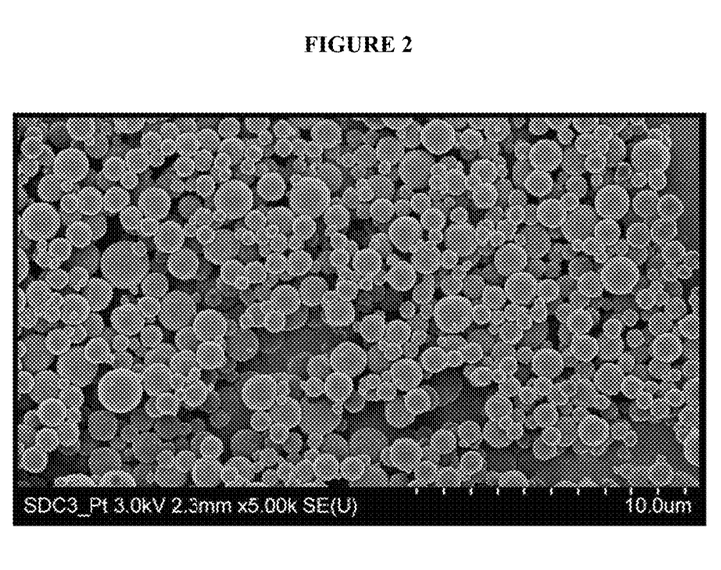
FIG. 2 shows collagen microparticles obtained by spray drying a solution of acid-soluble collagen (2.1 mg per mL) in acetic acid (0.5M) at 36° C.

A collagen solution is obtained in accordance with Example 1.1 with a concentration of 7 mg per mL. This solution is diluted in 500 mM acetic acid to obtain a final concentration of 2.1 mg per mL. Said solution is dried in an atomiser ("spray drier" Buchi B290). The rate of injection of the collagen solution, limited to 1 ml per minute, is controlled by an automatic syringe pump connected to the nozzle of the drying instrument. The temperature of the nozzle is held at 36° C., and the internal temperature of the system, measured between the drying column and the particle collection cyclone, is maintained throughout the process between 28 and 32° C. The flow of air responsible for the shearing of the droplets at the outlet of the nozzle is 1052 L per hour. The suction power, which controls the drying of the droplets between the outlet of the nozzle and the collector, is fixed at 75% of the maximum capacity of the drying system (30 m$^3$ per hour). The particles thus formed are collected by a high-performance cyclone. (FIG. 2).

Example 6: Analysis of Microparticles of Non-Denatured and Denatured Collagen Obtained by Spraying from a Solution of Acid-Soluble Collagen with a Concentration of 0.7 mg Par mL 6.1 Preparation of a Dry Powder of Non-Denatured Collagen According to the Invention.

A collagen solution is obtained in accordance with Example 1.1 with a concentration of 7 mg per mL. This solution is diluted in 500 mM acetic acid to obtain a final concentration of 0.7 mg per mL. Said solution is dried in an atomiser ("spray drier" Buchi B290). The rate of injection of the collagen solution, limited to 1 ml per minute, is controlled by an automatic syringe pump connected to the nozzle of the drying instrument. The temperature of the nozzle is held at 36° C., and the internal temperature of the system, measured between the drying column and the particle collection cyclone, is maintained throughout the process between 28 and 32° C. The flow of air responsible for the shearing of the droplets at the outlet of the nozzle is 1052 L per hour. The suction power, which controls the drying of the droplets between the outlet of the nozzle and the collector, is fixed at 75% of the maximum capacity of the drying system (30 $m^3$ per hour). The particles thus formed are collected by a high-performance cyclone.

Figure 7:
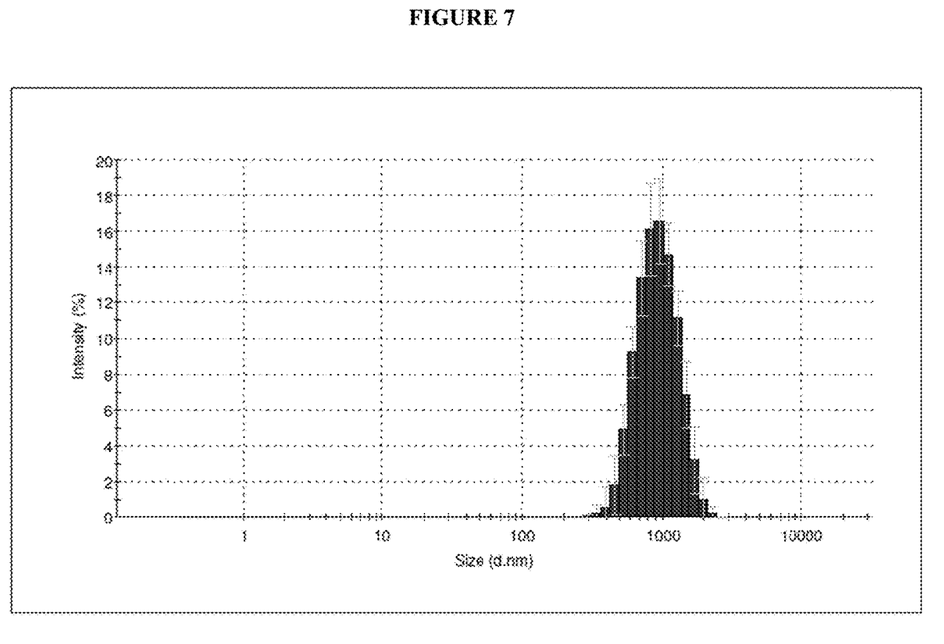
FIG. 7 shows the distribution of the diameter of the collagen coacervates 0.32 mg per mL according to Example 9, measured by dynamic light scattering.
Figure 8:
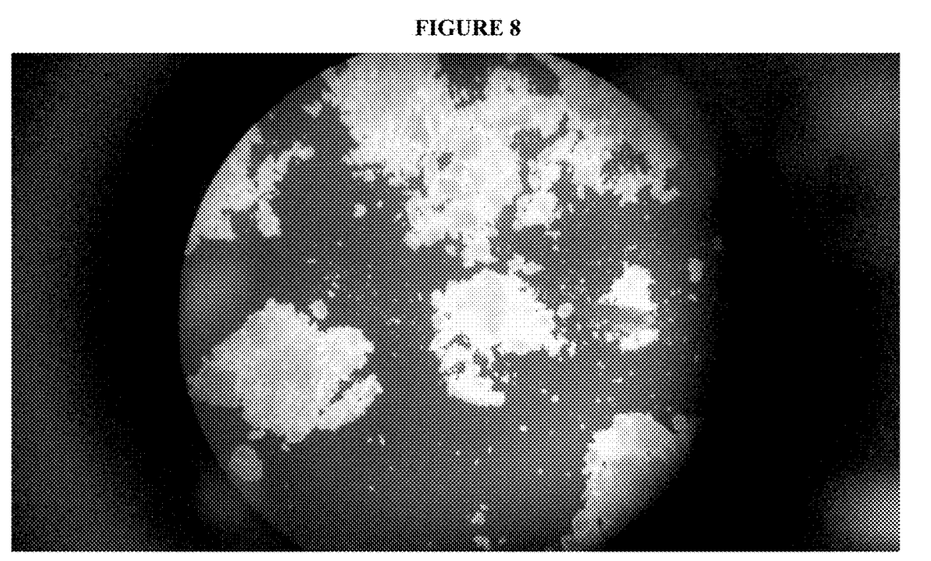
FIG. 8 is an image of a powdered composition according to the invention, recorded by polarised light microscopy.
Figure 9:
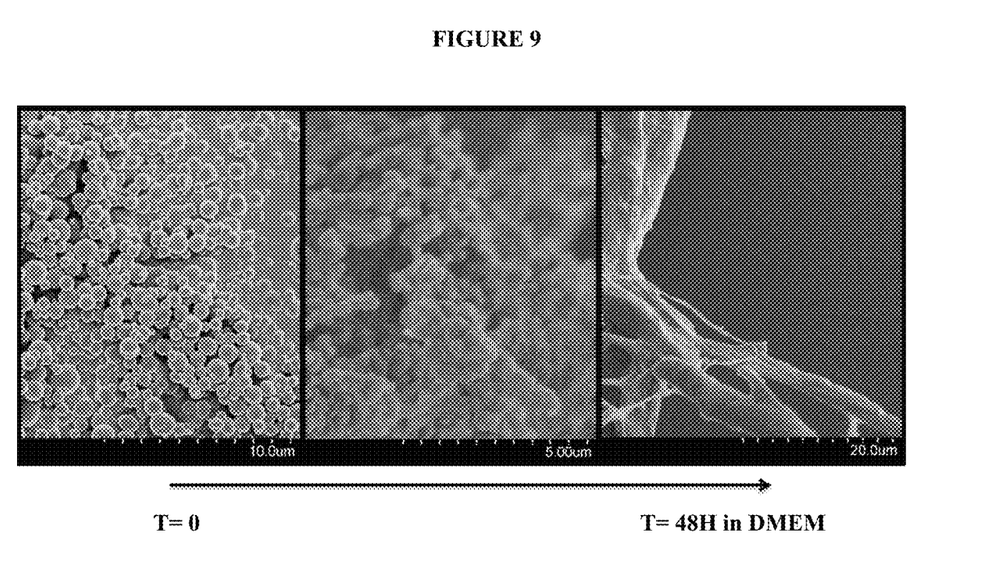
FIG. 9 shows different states of aggregation of a suspension comprising or consisting of a powdered composition according to the invention, in a culture medium Dulbecco 1X (DMEM), from t=0 to t=48H after contacting said suspension with the DMEM.

6.2 Preparation of a dry powder of denatured collagen not forming part of the invention. The collagen solution of Example 6.1 is dried in accordance with Example 6.1, with the temperature of the nozzle being the sole difference, maintained at 55° C. (FIG. 3).

Example 7: Injectable Solution of Collagen Coacervates Obtained in the Presence of Disodium Salt of ATP 7.1 Obtaining an Injectable Solution of Coacervates 250 µL, of an aqueous solution of disodium salt of 50 mM adenosine triphosphate are added to 1 mL of a collagen solution with a concentration of 7 mg par mL obtained in accordance with Example 1.1. The mixture thus obtained is stirred under vortex at 2400 revolutions per minute for 30 seconds. The cloudy suspension thus obtained is injected into a 70 µL PDMS mould.

7.2 Fibrillogenesis of the Suspension of Coacervates Induced by Exposure to Ammonia Vapours.

After injection of the suspension into the closed PDMS mould, the assembly is exposed to ammonia vapours to promote fibrillogenesis. After 24 hours, the gel thus formed is demoulded, with no significant change in volume (FIGS. 4 and 5).

Example 8: Injectable Suspensions of Coacervates of Collagen Obtained in the Presence of Disodium Salt of ATP 8.1 Obtaining an Injectable Suspension of Coacervates of Concentration 28 mg Par mL 200 µL, of an aqueous solution of disodium salt of 50 mM adenosine triphosphate are added to 1 mL of a collagen solution with a concentration of 7 mg par mL obtained in accordance with Example 1.1. The mixture thus obtained is stirred under vortex at 2400 revolutions per minute for 30 seconds. The cloudy suspension thus obtained is centrifuged for 2 minutes at 1700 g. A volume of 950 µL of supernatant is removed, and the pellet thus obtained stirred under a vortex so as to obtain a coacervate at a final concentration of 28 mg per mL. The coacervate thus obtained can be injected into a PDMS mould.

8.2 Obtaining an injectable suspension of coacervates of concentration 14 mg Per mL 200 µL, of an aqueous solution of disodium salt of 50 mM adenosine triphosphate are added to 1 mL of a collagen solution with a concentration of 7 mg par mL obtained in accordance with Example 1.1. The mixture thus obtained is stirred under vortex at 2400 revolutions per minute for 30 seconds. The cloudy suspension thus obtained is centrifuged for 30 seconds at 1700 g. A volume of 700 µL of supernatant is removed, and the pellet thus obtained stirred under a vortex so as to obtain a coacervate at a final concentration of 14 mg per mL. The coacervate thus obtained can be injected into a PDMS mould. The suspension obtained also can be injected into a type A gelatin gel (300 Bloom) dissolved 10% by mass in phosphate buffer.

8.3 Obtaining an Injectable Suspension of Coacervates of Concentration 5.8 mg Per mL 200 µL of an aqueous solution of disodium salt of 50 mM adenosine triphosphate are added to 1 mL of a collagen solution with a concentration of 7 mg par mL obtained in accordance with Example 1.1. The mixture thus obtained is stirred under vortex at 2400 revolutions per minute for 30 seconds. The cloudy suspension thus obtained has a final concentration of 5.8 mg per mL.

8.4 Obtaining an Injectable Suspension of Coacervates having a Concentration of 2.9 mg Per mL 500 µL of 500 mM acetic acid and 200 µL of an aqueous solution of disodium salt of 50 mM adenosine triphosphate are added to 500 µL of a collagen solution with a concentration of 7 mg par mL obtained in accordance with Example 1.1. The mixture thus obtained is stirred under vortex at 2400 revolutions per minute for 30 seconds. The cloudy suspension thus obtained has a final concentration of 2.9 mg per mL.

8.5 Obtaining an Injectable Suspension of Coacervates of Concentration 1.46 mg Par mL 750 µL of 500 mM acetic acid and 200 µL of an aqueous solution of disodium salt of 50 mM adenosine triphosphate are added to 250 µL it of a collagen solution with a concentration of 7 mg par mL obtained in accordance with Example 1.1. The mixture thus obtained is stirred under vortex at 2400 revolutions per minute for 30 seconds. The cloudy suspension thus obtained has a final concentration of 1.46 mg per mL.

8.6 Analysis of the Viscosity of the Coacervates Obtained and of Non-Coacervated Solutions of Acid-Soluble Collagen The viscosity of the suspensions of coacervates obtained in accordance with Examples 8.1 to 8.5 was measured in an Anton Parr MCR 302 rheometer in rotational viscometer mode using a cone-plane geometry. The viscosity was determined at shear rates from 1 to 100 $s^{-1}$. The viscosity of the suspensions of coacervate at a shear rate of 50 $s^{-1}$ was determined as 1.7 to 253 mPa·s for collagen concentrations from 1.45 to 28 mg per ml, respectively. The viscosity of solutions of acid-soluble collagen at concentrations from 1 to 7 mg per mL was also determined. The viscosity values obtained in accordance with the same analysis conditions vary between 16.8 mPa·s for a collagen concentration of 1 mg per mL and 217 mPa·s for a collagen concentration of 7 mg per mL. FIG. 6 combines the viscosity data as a function of the collagen concentration for the collagen solutions dissolved in 500 mM acetic acid and the collagen coacervates.

Example 9: Suspension of Collagen Coacervates Obtained in the Presence of Disodium Salt of ATP 9.1 Observation of an Injectable Suspension of Coacervates having a Concentration of 0.83 mg Per mL 100 µL of an aqueous solution of disodium salt of 50 mM adenosine triphosphate are added to 1 mL of a collagen solution with a concentration of 0.35 mg par mL obtained in accordance with Example 1.1. The mixture thus obtained is stirred under vortex at 2400 revolutions per minute for 30 seconds. The cloudy suspension thus obtained, with a final concentration of 0.32 mg per mL, is analysed by dynamic light scattering in a Zetasizer Nano S. apparatus. The diameter distribution of the particles determined in terms of intensity after 5 consecutive measurements is centred at 837 nm with a standard deviation of 21 nm (FIG. 7).

Example 10: Study in Vivo

A gel obtained from a suspension according to the present invention (for example according to example 2.3, 4.2 or 7.2) is implanted in vivo in the small animal (wistar rat) subcutaneously.
The following were evaluated:
a) the integration of the implants (absence of inflammation and colonisation by host cells leading particularly to the presence of endothelial cells);
b) limited absorption compared to reference implants (particularly diluted collagen and hyaluronic acid).
The lack of change in the volume of the implanted gel, for example on 15, 30 and 60 days after implantation, indicates that the gel is stable, in particular with respect to collagenases.

The invention claimed is:

1. An injectable suspension consisting of a powdered composition in an aqueous solution formed of water and acid or of a saline phosphate buffer,
wherein said powdered composition consists of spherical or spheroidal solid particles consisting of more than 90% by mass of non-denatured and uncrosslinked collagen, and less than 10% by mass of an aqueous solution formed of water and acid,
wherein a total collagen concentration is in a range of 20 to 200 mg per ml of suspension,
wherein a diameter of said spherical or spheroidal solid particles is in a range of 0.25 µm to 10 µm,
wherein the suspension forms dense fibrillar collagen matrices in vivo by assembly of collagen molecules of which the intermolecular distance is less than 10 nm, after being contacted with a physiological medium.

2. A cosmetic composition containing a suspension according to claim 1, said cosmetic composition further comprising one or more additives selected from anaesthetics, hyaluronic acid, elastins, vitamins and platelet rich plasma, ions, precursors of a mineral phase, proteoglycans, glycosaminoglycan, and non-fibrillar collagen types.

3. A pharmaceutical composition containing a suspension according to claim 1.

4. An injectable suspension consisting of a powdered composition in an acid-soluble collagen acidic aqueous solution,
wherein said powdered composition consists of spherical or spheroid solid particles consisting of more than 99% by mass of non-denatured and uncrosslinked collagen, and less than 1% by mass of an aqueous solution formed of water and acid,
wherein a diameter of said spherical or spheroid solid particles is in a range of 0.25 µm to 10 µm,
wherein the total collagen concentration is greater than 20 mg per ml of suspension, and
wherein the suspension forms dense fibrillar collagen matrices in vivo by assembly of collagen molecules of which the intermolecular distance is less than 10 nm, after being contacted with a physiological medium.

5. An injectable suspension consisting of a powdered composition in an acid-soluble collagen acidic aqueous solution,
wherein said powdered composition consists of spherical or spheroid solid particles consisting of more than 99% by mass of non-denatured and uncrosslinked collagen, and less than 1% by mass of an aqueous solution formed of water and acid,
wherein a diameter of said spherical or spheroid solid particles is in a range of 0.25 µm to 10 µm,
wherein the total collagen concentration is greater than 100 mg per ml of suspension, and
wherein the suspension forms dense fibrillar collagen matrices in vivo by assembly of collagen molecules of which the intermolecular distance is less than 10 nm, after being contacted with a physiological medium.

6. The suspension according to claim 1, wherein the acid present in said powdered composition is acetic acid.

* * * * *